United States Patent
Erani

(10) Patent No.: US 9,186,312 B2
(45) Date of Patent: *Nov. 17, 2015

(54) COMPOSITIONS AND METHODS FOR SKIN TREATMENT

(76) Inventor: Simon Erani, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,742

(22) Filed: Aug. 27, 2012

(65) Prior Publication Data

US 2013/0102540 A1 Apr. 25, 2013

Related U.S. Application Data

(63) Continuation of application No. 12/895,940, filed on Oct. 1, 2010, now Pat. No. 8,263,654, which is a continuation of application No. 09/922,233, filed on Aug. 3, 2001, now Pat. No. 7,834,057.

(60) Provisional application No. 60/222,895, filed on Aug. 3, 2000.

(51) Int. Cl.
| | |
|---|---|
| *A61K 38/00* | (2006.01) |
| *A61K 8/64* | (2006.01) |
| *A61K 8/67* | (2006.01) |
| *F42B 5/30* | (2006.01) |
| *A61Q 19/00* | (2006.01) |
| *A61Q 19/08* | (2006.01) |

(52) U.S. Cl.
CPC ... *A61K 8/64* (2013.01); *A61K 8/67* (2013.01); *A61K 8/675* (2013.01); *A61K 8/676* (2013.01); *A61K 8/678* (2013.01); *A61Q 19/00* (2013.01); *A61Q 19/08* (2013.01); *F42B 5/30* (2013.01)

(58) Field of Classification Search
CPC ....... A61K 8/64; A61K 31/19; A61K 31/215; A61K 31/07; A61K 31/11; A61K 38/00; A61K 8/02; A61K 8/18; A61K 8/67; A61K 8/678; A61K 8/675; A61K 8/676
USPC .................... 514/557, 570, 529, 703, 725, 12
See application file for complete search history.

(56) References Cited

U.S. PATENT DOCUMENTS

2002/0025303 A1* 2/2002 Fructus et al. ............. 424/78.03

OTHER PUBLICATIONS

Brooks Industries Inc. cosmetic Ingredients & Ideas. Vitazymes Protein Bonded Vitamins 1993.*

* cited by examiner

*Primary Examiner* — Jennifer M Kim
(74) *Attorney, Agent, or Firm* — Goldberg Cohen LLP

(57) ABSTRACT

Compositions for the treatment of the skin. The compositions reduce and/or reverse the visible appearance of skin damage. In the preferred embodiment, the composition includes Retinyl Palmitate Polypeptide; Ascorbylmethylsilanol Pectinate; Tocopheryl Polypeptide; Cholecalciferol Polypeptide; and Niacinamide Polypeptide.

1 Claim, No Drawings

COMPOSITIONS AND METHODS FOR SKIN TREATMENT

RELATED APPLICATIONS

This application is a continuation of U.S. application Ser. No. 12/895,940 filed Oct. 1, 2010 now U.S. Pat. No. 8,263,654, which is a continuation of U.S. application Ser. No. 09/922,233 filed Aug. 3, 2001 (patented, U.S. Pat. No. 7,834,057), which claims the benefit of U.S. Provisional Application Ser. No. 60/222,895 filed Aug. 3, 2000. The priority of all of those applications is claimed, and the contents of all of those applications are hereby fully incorporated into this application by reference.

FIELD OF INVENTION

The present inventions are directed to compositions and methods for the treatment of skin, including compositions and methods of countering the effects of sun damage and aging.

BACKGROUND OF THE INVENTION

The skin is considered the largest organ of the human body and has numerous different functions, including, for example, thermoregulation, protection, metabolic functions and sensation. As the outermost barrier of an organism, however, it is continually subjected to damages from causes such as ultraviolet light, contaminants, stress, and so forth. Over time, both environmental and genetic factors can contribute to visible skin damage.

As is well known, a large number of products have been introduced to the market to reduce such skin damage and/or its appearance, and even to reverse it to the extent possible. It is an important objective in the art to develop and introduce new and improved compositions for application to the skin to better achieve those objectives.

Throughout this application, trademarks and trade names are identified using a "TM" notation.

SUMMARY OF THE INVENTION

It is an object of the present invention to provide compositions for skin treatment.

It is a further object of the present invention to provide compositions for improving the appearance of the skin.

It is a further object of the present invention to provide methods for tracking skin damage and the reversal thereof.

In accordance with the invention, compositions are provided for the treatment of the skin to reduce and/or reverse the visible appearance of skin damage, and to provide younger, healthier looking skin. In the preferred embodiment, the composition includes one to five of the following active components for topical application: Retinyl Palmitate Polypeptide; Ascorbylmethylsilanol Pectinate; Tocopheryl Polypeptide; Cholecalciferol Polypeptide; and Niacinamide Polypeptide. Preferably all five are utilized in combination to achieve best results.

In further embodiments of the invention, additional compositions and regimens for skin treatment are provided. In yet further embodiments, a method is provided for tracking and monitoring damage to the skin occurring over time.

Further objects and features of the invention will become apparent in conjunction with the disclosure herein.

DETAILED DESCRIPTION OF THE INVENTION AND THE PREFERRED EMBODIMENTS

In accordance with the present invention new skin treatment compositions are provided for improving the appearance of the skin. The compositions herein have been found to demonstrate significant effectiveness in reducing and/or reversing the visible appearance of skin damage and imperfections, to provide the appearance of younger, healthier skin, when applied topically.

In accordance with the invention, the composition includes Retinyl Palmitate Polypeptide, Ascorbylmethylsilanol Pectinate, Tocopheryl Polypeptide, Cholecalciferol Polypeptide, and/or Niacinamide Polypeptide. It is desirable that these particular components are utilized, as opposed to other forms of Vitamin A, Vitamin C, etc., due to the fact that they have been found to produce significantly superior results. A suitable supplier for these components is Brooks Industries, Inc. of South Plainfield, N.J.

In one embodiment of the invention, at least one of these components is topically applied to the skin. In the preferred embodiments of the invention, however, two to five of these components are applied to achieve more effective results. Those two or more components can be mixed in any levels desired to achieve improvements in skin appearance, although preferred formulations are disclosed below.

In the preferred embodiment of the invention (referred to herein as MDT-5), a composition is provided including all five of the treatment components are included. The five components of MDT-5 can be mixed in any desired levels, although they are preferably provided in the relative proportions shown in Table 1a.

Table 1—Molecule Dispersion Technology (MDT) Formulations

TABLE 1a

| MDT-5 | |
| --- | --- |
| Retinyl Palmitate Polypeptide | 95% |
| Ascorbylmethylsilanol Pectinate | 1.25% |
| Tocopheryl Polypeptide | 1.25% |
| Cholecalciferol Polypeptide | 1.25% |
| Niacinamide Polypeptide | 1.25% |

In an alternate embodiment (MDT-5H), the components are provided in the relative proportions shown in Table 1b:

TABLE 1b

| MDT-5H | |
| --- | --- |
| Retinyl Palmitate Polypeptide | 89.75% |
| Ascorbylmethylsilanol Pectinate | 5.00% |
| Tocopheryl Polypeptide | 2.50% |
| Cholecalciferol Polypeptide | 1.25% |
| Niacinamide Polypeptide | 1.50% |

In a further alternate embodiment (MDT-10), the components are provided in the relative proportions shown in Table 1c:

TABLE 1c

| MDT-10 | |
| --- | --- |
| Retinyl Palmitate Polypeptide | 1.5% |
| Ascorbylmethylsilanol Pectinate | 5% |
| Tocopheryl Polypeptide | 2.5% |

TABLE 1c-continued

| MDT-10 | |
|---|---|
| Cholecalciferol Polypeptide | 0.5% |
| Niacinamide Polypeptide | 1.5% |
| Pantothenic Polypeptide | 1.5% |
| BIOPEPTIDE EL ™ (Palmitoyl Oligopeptide) | 3% |
| Abnfeltia Concinna ("APT") | 2% |
| Beta Glucan in aloe vera carrier | 1.0% |
| Hyaluronic Acid (0.5%) | 3.0% |

It has been found that use of a composition with all five components of MDT is preferred, as due to their synergistic effect when combined. In alternate embodiments of MDT, however, a composition can be provided which contains from two to five of the components shown in Table 1d. In these alternate embodiments, a wide range of concentrations of each component can be utilized consistent with the invention. In all of the formulations disclosed in the present application, the total percentage is, of course, intended to sum to 100%. Each variation or range shown is intended to represent the allowable variation for any individual component within the composition. For example, in Table 1d, in a pure mixture of the components disclosed, if Retinyl Palmitate Polypeptide is 20% of the formulation, one to four of the remaining components make up the remaining 80%.

TABLE 1d

| MDT Variations (one to five of the following components) | |
|---|---|
| Retinyl Palmitate Polypeptide | Range: 0.01%-100% |
| Ascorbylmethylsilanol Pectinate | Range: 0.01%-100% |
| Tocopheryl Polypeptide | Range: 0.01%-100% |
| Cholecalciferol Polypeptide | Range: 0.01%-100% |
| Niacinamide Polypeptide | Range: 0.01%-100% |

In addition, each component can be used in the above ranges, with or without any of the other ingredients listed in the present application (e.g. in Tables 2-8) or any combination of those other ingredients.

Consistent with the invention, a composition may be applied to the skin wherein the composition consists of pure MDT-5 or a pure form of one of the other MDT formulations provided above. Preferably, however, a creme, lotion, gel, or other substance is applied to the skin wherein the substance includes a percentage of one of the MDT compositions therein (preferably MDT-5), as opposed to application of pure MDT. In the preferred embodiment, the topical application is 2%-5% MDT (MDT-5 in particular). Such levels of MDT have been found to provide very effective reversal of the appearance of skin damage, yet at a reasonable cost.

In alternate embodiments, the substance includes an MDT formulation wherein the substance contains approximately 1%-10% MDT. In a further alternate embodiment, a substance which is 10%-20% MDT is used. This latter formulation is highly effective, and constitutes one of the preferred embodiments; however, a higher cost is associated with use of MDT at this more potent level. In further alternative embodiments, the composition can have any other percentage of MDT or MDT-5 desired, e.g. as low as 0.01% or lower, up to as high as 100% pure MDT or MDT-5.

In further embodiments of the invention, the MDT formulation is provided in a substance such a cream, lotion, or gel, with one or more other active ingredient. One active ingredient which has been found to be particularly useful with the MDT formulations is glycolic acid. In a preferred embodiment of an MDT/glycolic acid mixture, the cream, lotion, gel, or so forth includes approximately 1.5% MDT or MDT-5, and 3% glycolic acid (although other relative proportions are effective as well). However, addition of glycolic acid is to be limited to the compositions containing lower percentages of MDT; higher concentrations such as the 10% or 20% MDT composition are preferably utilized without glycolic acid as the combination may potentially result in skin irritation.

Various preferred embodiments of the present invention, including both mixtures of MDT-5 with other components, or other skin treatment compositions, are further provided in Tables 2 through 7. For example, the embodiment of Table 2 is an MDT-5 product, while the embodiment of FIG. 3 is another desirable product, which does not include the components of MDT-5, although MDT-5 can be added to it if desired.

TABLE 2

| Formulas A-1, A-2 and A-3 ("A-Bomb ™") | |
|---|---|
| Formula A-1: 2% MDT (preferably MDT-5) | |
| Formula A-2: 5% MDT (preferably MDT-5) | |
| Formula A-3: 10% MDT (preferably MDT-5) | |
| Ingredients: | |
| Water | 70-90% |
| Glycerin | 2.5% |
| Myristyl Myristate | 2.5% |
| MDT: | 1-10% |
| PEG-8 Distearate | 1-3% |
| Glyceryl Stearate/PEG-100 Stearate | 2-5% |
| PEG-40 Stearate | 0.5-3% |
| Sorbitan Stearate | 0.5-3% |
| Cetyl Alcohol | 0.5-3% |
| Carbomer | 0.2-0.8% |
| Hydroxyethylcellulose | 0.1-0.5% |
| Triethanolamine | 0.2-0.6% |
| Diazolidinyl Urea | 0.3% |
| Methylparaben | 0.2% |
| Propylparaben | 0.1% |
| Tetrasodium EDTA | 0.1-0.2% |
| Palma Rosa Extract | 0.5-5% |
| Ylang Ylang Extract | 0.5-5% |
| Jasmine Extract | 0.5-5% |
| Geranium Extract | 0.5-5% |
| Lavender Extract | 0.5-5% |
| Marigold Extract | 0.5-5% |
| Galbanum Extract | 0.5-5% |
| DMDM Hydantoin | 0.05-0.1% |
| Iodopropynyl Butylcarbamate | 0.05-0.1% |

TABLE 3

| Formula H-1("H-Bomb" ™) | | |
|---|---|---|
| Water | 60-99.9% | Preferred 70-90% |
| Cyclomethicone | 2.0-5.0% | |
| Glycolic Acid: | 0.1-20.0% | |
| Glycerine | 2.0-5.0% | |
| $C_{12}$-15 Alkyl Octonoate | 2.0-5.0% | |
| Stearyl Alcohol | 2.0-5.0% | |
| Ceteareth-20 | 2.0-5.0% | |
| Aluminum Starch Octenylsuccinate | 2.0-5.0% | |
| Propylene Glycol | 2.0-5.0% | |
| PEG-40 Stearate | 1.0-3.0% | |
| Petrolatum | 1.0-3.0% | |
| Glyceryl Stearate | 1.0-3.0% | |
| Retinyl Palmitate Polypeptide: | 1.50% | Preferred: 1.5 & 2.0%; Range: 0.5-100% |
| Shea Butter | 1.0-3.0% | |
| Sorbitan Stearate | 0.5-3% | |
| Stearic Acid | 1.0-3.0% | |
| Dimethicone | 1.0-3.0% | |
| Methyl Glucose Sesquistearate | 1.0-3.0% | |
| Ammonium Glycolate | 0.5-3% | |
| PEG-20 Methyl Glucose | 1.0-3.0% | |

TABLE 3-continued

Formula H-1 ("H-Bomb" ™)

| | | |
|---|---|---|
| Sesquistearate | | |
| Magnesium Aluminum Silicate | 0-1% | |
| Lanolin Alcohol | 0-1% | |
| Stearamidopropyl Dimethylamine | 0-1% | |
| Isostearic Acid | 0-1% | |
| Polysorbate 20 | 0-1% | |
| Diazolidinyl Urea | 0.3% | |
| Xanthan Gum | 0.3% | |
| Sorbic Acid | 0.09% | |
| Tetrasodium EDTA | 0.1-0.2% | |
| Allantoin | 0.10% | |
| Simethicone | 0.09% | |
| Orange Extract | 0.01% | 0.01-5% |
| Palma Rosa Extract | 0.01% | 0.01-5% |
| Lime Extract | 0.01% | 0.01-5% |
| Lavender Extract | 0.10% | 0.01-5% |
| Oak Moss Extract | 0.10% | 0.01-5% |
| Galbanum Extract | 0.10% | 0.01-5% |

TABLE 4

Formula M-1 ("Multi-Vitamin Skin Solution")

| | |
|---|---|
| Water | 40-70% |
| BIOPEPTIDE EL ™ | 3.0% |
| (Palmitoyl Oligopeptide) | |
| APT | 2.0% |
| Vitamin A Polypeptide | 1.5% (Retinyl Palmitate Polypeptide) |
| Vitamin B3 Polypeptide | 1.5% (Niacinamide Polypeptide) |
| Vitamin B5 Polypeptide | 1.5% (Pantothenic Acid Polypeptide) |
| Ascorbylmethysilanol | 5.0% (Vitamin C) |
| Vitamin E Polypeptide | 2.5% (Tocopherol Polypeptide) |
| Vitamin D Polypeptide | 0.5% (Cholecalciferol Polypeptide) |
| Beta Glucan in Aloe Vera Carrier | 1.0% |
| Hyaluronic Acid (0.5%) | 3.0% |
| Peg-40 Stearate | 2-5% |
| Sorbitan Stearate | 2-5% |
| Carbomer | 0.2-0.5% |
| Methylparaben | 0.2% |
| Propylparaben | 0.1% |
| Diazolidinyl Urea | 0.3% |
| Tetra Sodium EDTA | 0.1-0.2% |
| Trie Thanolamine | 0.2-0.5% |
| Cetyl Alcohol | 2-5% |
| Glycerin | 2-5% |
| DMDM Hydontoin | 0.05-0.1% |
| Iodopropynyl Butylcarbmate | 0.05-0.1% |

TABLE 5

Formula SF-1 ("Safe Face ™" SPF-30 UVA & UVB Protection)

Active Ingredients:

| | | |
|---|---|---|
| Ethylhexyl Methoxycinnamate | Preferred: 6.00% | Range: 1-100% |
| Octyl Salicylate | Preferred: 3.00% | Range: 1-100% |
| Butyl Methoxydibenzoylmethane | Preferred: 2.00% | Range: 1-100% |
| MDT (pref. MDT-5) | Preferred: 1-10% | |

This formulation also contains a sunscreen, such as, for example, any of the sunscreen (sunblock) formulations currently available on the market. In one embodiment, for example, the ingredients include:

| | |
|---|---|
| Water | 60-99.9% |
| Glycerine | 2.5% |
| PEG-40 Stearate | 2.5% |
| Bis-Diglyceryl Polyacyladipate-2 | 2.0-5.0% |
| C12-15 Alkyl Benzoate | 2.0-5.0% |
| Dipropylene Glycol Dibenzoate | 1.0-3.0% |
| PPG-15 Stearyl Ether Benzoate | 1.0-3.0% |
| Stearyl Alcohol | 1.0-3.0% |
| Ceteareth-20 | 1.0-3.0% |
| Methyl Glucose Sesquistearate | 1.0-3.0% |
| Peg-20 Methyl Glucose Sesquistearate | 1.0-3.0% |
| Sorbitan Stearate | 1.0-3.0% |
| Green Tea Extract | 0-1% |
| Chamomile Exrtract | 0-1% |
| Panthenol | 0-1% |
| Carbomer | 0-1% |
| Triethanolamine | 0-1% |
| Diazolidinyl Urea | 0-3% |
| Methylparaben | 0-1% |
| Proplyparaben | 0-1% |
| Tetrasodium EDTA | 0-1% |
| Allantoin | 0-1% |
| Palma Rosa Extract | 0.01% |
| Ylang Ylang Extract | 0.01% |
| Jasmine Extract | 0.01% |
| Geranium Extract | 0.01% |
| Lavender Extract | 0.01% |
| Marigold Extract | 0.01% |
| Galbanum Extract | 0.01% |

TABLE 6

Formulas T-1, T-2 and T-3 ("Transport ™")
Formula # T-1: 2% MDT
Formula # T-2: 5% MDT
Formula # T-3: 10% MDT

| | | |
|---|---|---|
| Water | Preferred: 80-90% | |
| Glycolic Acid | Preferred: 3.5%, 5%, 10%, 15% | Range: 1.0-70% |
| Polysorbate 20 | 2-4% | |
| Green Tea Extract | 1-5% | |
| Ethoxydiglycol | 1-5% | |
| Ammonium Glycolate | 1-2% | |
| MDT (pref. MDT 5) | Preferred: 1-10% | |
| Panthenol | .1-1% | |
| Chamomile Extract | .1-1% | |
| Aloe Powder | .1-1% | |
| Menthol | .001-.1% | |
| Tetrasodium EDTA | .1-.2% | |
| Methylchloroisothiazolinone | .05-.1% | |
| Methylisothiazolinone | .05-.1% | |
| Grapeseed Extract | .05-.5% | |
| Palma Rosa Extract | .01% | |
| Ylang Ylang Extract | .01% | |
| Jasmine Extract | .01% | |
| Geranium Extract | .01% | |
| Lavender Extract | .01% | |
| Marigold Extract | .01% | |
| Galbanum Extract | .01% | |

TABLE 7

Formulas S-1, S-2 and S-3 ("Serum™")
Formula # S-1: 2% MDT
Formula # S-2: 5% MDT
Formula # S-3: 10% MDT

| | | |
|---|---|---|
| Water | 60-80% | |
| Ascorbylmethylsilanol | Preferred: 5%, 10%, 15%, 20%, 60% | Range: 1-100% |
| SD Alcohol 40 | 5-15% | |
| Propylene Glycol | 2-7% | |
| MDT (pref. MDT 5) | 1-10% | |
| Xanthan Gum | .3-1.0% | |
| Orange Extract | .05-.5% | |
| Palma Rosa Extract | .05-.5% | |
| Lime Extract | .05-.5% | |
| Lavender Extract | .05-.5% | |
| Oak Moss Extract | .05-.5% | |
| Galbanum Extract | .05-.5% | |

TABLE 7-continued

Formulas S-1, S-2 and S-3 ("SerumTM")
Formula # S-1: 2% MDT
Formula # S-2: 5% MDT
Formula # S-3: 10% MDT

| | |
|---|---|
| Diazolidinyl Urea | .3% |
| Methylparaben | .1% |
| Propylparaben | .05% |
| Tetrasodium EDTA | .1-.2% |

Other active ingredients which can be mixed with MDT or MDT-5 are provided in Table 8. One or more of the ingredients listed in Table 8 can be combined with MDT (particularly MDT-5), to provide further preparations for topical application to the skin. These ingredients can be included at any level desired, although preferred ranges are listed in the table.

TABLE 8

Additional Active Ingredients

| Ingredient | Range |
|---|---|
| Lactic Acid- | .1-99.99% |
| Salicylic Acid- | .1-99.99% |
| BIOPEPTIDE EL ™ (Palmitoyl Oligopeptide)- | 1.0-99.99% |
| APT- | 1.0-99.99% |
| Beta Glucan in Aloe Vera Carrier- | 1.0-99.99% |
| Hyaluronic Acid- | 3.0-99.99% |
| Ascorbyl Palmitate (C Ester)- | .1-99.99% |
| NAB Fennel Seed Extract- | 1-99.99% |
| Water & P-hospholipids & Superoxide Dismutase- | 5.0-99.99% |
| Superoxide Dismutase- | .1-99.99% |
| Ascorbic Acid Polypeptide- | .5-99.99% |
| *Saccharomyces* Lysate Extract- | .5-1.0% |
| Water & *Saccharomyces* Lysate Extract | 2.0-4.0% |
| Water & Phospholipids & *Saccharomyces* Lysate Extract- | 5.0-15.0% |
| Silicon & Zinc & Copper & Iron & Magnesium Yeast Glycopeptide- | .1-2.0% |
| 5% Solution of Biomin Cinque- | .5-5.0% |
| Water & Butylene Glycol & *Saccharomyces*/Calcium Ferment- | .5-5.0% |
| Water & Butylene Glycol & *Saccharomyces*/Copper Ferment- | .5-5.0% |
| Water & Butylene Glycol & *Saccharomyces*/Germanium Ferment- | .5-5.0% |
| Water & Butylene Glycol & *Saccharomyces*/Iron Ferment- | .5-5.0% |
| Water & Butylene Glycol & *Saccharomyces*/Maganese Ferment- | .5-5.0% |
| Water & Butylene Glycol & *Saccharomyces*/Magnesium Ferment- | .5-5.0% |
| Water & Butylene Glycol & *Saccharomyces*/Selenium Ferment- | .5-5.0% |
| Water & Butylene Glycol & *Saccharomyces*/Silicon Ferment- | .5-5.0% |
| Water & Butylene Glycol & *Saccharomyces*/Zinc Ferment- | .5-5.0% |
| Water & Aloe Extract & Yeast Extract- | 5.0-10.0% |
| Milk Protein & Plant Lipids & Plant Carbohydrates- | 1.0-5.0% |
| Water & Bilberry Extract & Sugar Cane Extract & Sugar Maple Extract & Orange Extract & Lemon Extract- | 5.0-15.0% |
| Water & Willow Bark Extract & Phospholipids- | 5.0-10.0% |
| Water & Phospholipids & Bladderwrack Extract & Ivy Extract & Horsechestnut Extract- | 1.0-5.0% |
| Phospholipids & Aloe Vera Gel- | 1.0-5.0% |
| Squalane & Squalene & Glycolipids & Phytosterol & Tocopherol- | .5-10.0% |
| Water & Phospholipids & Evening Primrose Oil- | 1.0-5.0% |
| Soybean Extract & Ceramide 3- | 1.0-4.0% |
| Barley Oligosaccharides- | 2.0-10.0% |
| Soy Dihydroxypropyldimonium Polyglucose & Propylene Glycol- | .5-10.0% |
| Water & Panthenol & Phospholipids- | 2.0-10.0% |
| Water & Phospholipids & Tocopherol & Retinyl Palmitate Acetate & Ascorbyl Palmitate- | 5.0-10.0% |
| Acrylate/Carbamate Copolymer & Lactic Acid- | .2-2.0% |
| Phosphoglycoproteins Water & Phospholipids & Glycoproteins- | 1.0-10.0% |
| Soluble Collagen (Mwt: 4,000)- | 1.0-10.0% |
| Hydrolyzed Elastin (Mwt: 4,000)- | .5-4.0% |
| Hydrolyzed Collagen- | .2-25.0% |
| Collagen Amino Acids (Mwt: 200)- | 1.0-5.0% |
| Glyceryl Collagenate- | .5-5.0% |
| Eleseryl SH SHT- | 3.0-10.0% |
| Liposomes Anti-Age- | 5.0-15.0% |
| Seanamin AT- | 3.0-5.0% |
| Tissulan- | 2.0-5.0% |
| Vegeles WP SP- | 3.0-10.0% |
| Vegeseryl HGP LP- | 3.0-10.0% |
| Keratolan- | 1.0-5.0% |
| Lactolan- | 2.5-10.0% |
| Lipodermol- | 1.0-3.0% |
| Melhydran- | 3.0-7.0% |
| Oceagen- | 1.0-5.0% |
| Prolactyl- | 3.0-10.0% |
| Seanamin Su- | 5.0-8.0% |
| Seanamin TH- | 3.0-5.0% |
| Technobion- | 5.0-10.0% |
| Cytokinol- | .5-2.0% |
| Dermosaccharides GY- | 1.0-5.0% |
| Dermosaccharides HC- | 1.0-3.0% |
| Dermosaccharides SEA- | 1.0-3.0% |
| Seanamin MY- | 5.0-8.0% |
| Technobion- | 2.0-8.0% |
| Vitacell- | 2.0-5.0% |
| Ceramides- | 0.3-1.0% |
| Helioceram- | 0.3-0.7% |
| Lipodermol- | 1.0-3.0% |
| Sealipids- | 1.0-3.0% |
| Sphingoceryl Fluid- | 2.0-5.0% |
| Sphingoceryl Powder- | 2.0-20.0% |
| Sphingoceryl VEG- | 2.0-5.0% |
| Sphingoceryl WAX- | 0.5-3.0% |
| Sphingosome AL- | 3.0-7.0% |
| WS-Ceramides- | 2.0-10.0% |
| Biophytex- | 3.0-5.0% |
| Lipo-Biophytex- | 3.0-5.0% |
| Peridermin- | 3.0-5.0% |
| Rhizodermin- | 3.0-7.0% |
| Sphingosome AL- | 3.0-5.0% |
| Vegeles CPS- | 2.0-7.0% |
| Vegeles SR- | 3.0-5.0% |
| A.F.R.- | 3.0-5.0% |
| Endonucleine- | 3.0-5.0% |
| Oleo-A.F.R.- | 2.0-3.0% |
| Vegeles PF- | 2.0-3.0% |
| Dermosaccharides- | 1.0-3.0% |
| Firmogen- | 2.0-10.0% |
| Laricyl- | 3.0-10.0% |
| Oceagen- | 2.0-5.0% |
| Prosyncoll- | 0.5-2.0% |
| Seanamin BD- | 0.5-3.0% |
| Seanamin SU- | 3.0-5.0% |
| Vegeseryl- | 3.0-10.0% |
| Bioslimex- | 3.0-5.0% |
| Liposomes Slimmigen- | 5.0-7.0% |
| Seanamin BD- | 0.5-3.0% |
| Slimmigen- | 3.0-7.0% |
| Asebiol- | 3.0-5.0% |
| Vegeles AHA- | 2.0-5.0% |
| Alpha Lipoic Acid- | .1-99.99% |
| DMAE- | .1-99.99% |
| Vitamin E Acetate | .1-99.99% |
| Vitamin E Alcohol | .1-99.99% |
| Vitamin A Palnitate | .1-99.99% |
| Vitamin B5 Pathenol | .1-99.99% |

It should be noted that, in some of the tables, the ingredients and ranges provided for the formulas include ranges for materials which are non-active ingredients. The provision of a range or level for a material is not meant to suggest or indicate that the material is necessarily an active ingredient or that the formulas are necessarily limited to those ranges.

Rather any suitable level can be utilized, especially for the non-active ingredients. For example, in the composition of Table 5, any suitable sunblock can be used as an alternative to or in addition to the active ingredients listed.

Likewise, in all of the above formulations, the potency of the MDT can be varied as discussed above. If desired, the MDT can be from approximately 0.01%-99% of the total composition, although preferred levels are 1-5%, 5-10%, 10-20%, or approximately 2%, 5% or 10%.

In a further preferred embodiments of the present invention, various alternative skin care methods or regimens are provided, as shown in the Tables 9a-9e. According to these regimens, a sequence of products are applied to the skin as shown below.

TABLE 9

Preferred Skin Care Regimens
9a: Regimen 1

1) Glycolic Acid pads (3-20%)
2) Ascorbylmethylsilanol Pectinate (3-70%)
3) "A-Bomb" 0.5-70%

The above can be used in any order and can be applied in separate steps, or in a product (pads, lotions, or so forth) containing all three of the above. In addition, each one of the above three preferably has an MDT compound added, although, alternatively, one or more can be provided without MDT. In a further alternative embodiment, the three compounds are utilized, even if none of them include an MDT compound (or MDT related compound), although the use of an MDT compound (or MDT related compound) is preferred.

9b: Regimen 2

Direct application of an MDT (e.g. MDT-5, MDT-5H or MDT10) compound or MDT related compound to the skin.

9c: Regimen 3

1) An MDT (e.g. MDT-5, MDT-5H or MDT10) compound or MDT related compound.
2) Glycolic Acid pads (2%-20%)
3) Vitamin C serum (5-70%)
4) "A Bomb" 0.5-50%

The above can be used in any order and can be applied in separate steps, or in a product (pads, lotions, or so forth) containing all three of the above. Compounds 2-4 can include an MDT or MDT related compound, or be free of any MDT or MDT related compounds. In the preferred embodiment, one or more (preferably all) of 2-4 include an MDT or MDT related compound.

| 9d: Regimen 4 | | |
| --- | --- | --- |
| Step 1- | A cleanser | |
| Step 2- | Transport No. 5, No. 10, No. 15 | Range: 0.1-100% |
| Step 3- | Serum No. 10, No. 20, No. 60 | Range: 0.1-100% |
| Step 4- | A Bomb No. 2, No. 5, No. 10 | Range: 0.1-100% |
| Step 5- | Safe Face | |

Preferably the products in the above embodiment are provided in the order disclosed above, although any other order of applications can be used as well.

9e: Regimen 5

In a further alternative or additional regimen, a consumer utilizes 4% glycolic acid pads, followed by 10% stabilized Vitamin C (in the form of Ascorbylmethysilanol or Ascorbylmethysilanol Pectinate), followed by 2% Vitamin A cream (i.e. "A-bomb"). This regimen is preferably provided in addition to or in conjunction with the use of products containing an MDT or MDT related compound of the present invention.

In a further alternative embodiment, 10% glycolic acid pads (with or without MDT or an MDT related compound), 20% stabilized Vitamin C (with or without MDT or an MDT related compound), and 10% A-bomb (with or without MDT or an MDT related compound) are provided.

In a further embodiment, 2-50 glycolic acid pads (with or without MDT or an MDT related compound), 2-99% stabilized Vitamin C (with or without MDT or an MDT related compound), and 0.5-99% A-bomb (with or without MDT or an MDT related compound) are provided.

For any of the above, the compounds can be applied separately (preferably in this order, although any order can be used), or a product can be provided combining all three of these materials.

In a further embodiment of the invention, consumers are provided with the ability to objectively monitor, record and verify the effectiveness of skin care products on their skin, preferably at the same location that they purchase those skin care products. This monitoring can be conducted of any skin care product, but is preferably conducted of the products of the present invention in particular to demonstrate and memorialize their effectiveness.

In accordance with the method, a retail store or other commercial location is provided where a consumer can have an image taken of the condition of his or her skin. Preferably, this store or location is the same location where the consumer can go to purchase his or her skin care products. Further preferably, the consumer can purchase MDT products of the invention (or one of the other embodiments disclosed above) at that location.

At the retail location, images of the consumer's skin are taken with a camera. Preferably, the imaging begins before the first use of the skin treatment composition or skin care product. Over time, the consumer returns periodically to the store to purchase additional product. Preferably, each time more product is purchased additional images are taken of the skin (although images can also be taken between purchases or without any concurrent purchase), so as to create an ongoing record of the skin's appearance over time.

Thus, in this embodiment of the invention, consumers can easily monitor, track and record the continuing condition of their skin as they use particular skin care products. This tracking verifies whether or not the products are effective with records that demonstrate any changes in skin appearance and document the reduction and/or reversal of the appearance of damage or other imperfections. Furthermore, the consumer is provided with objective evidence in the form of photographs showing skin changes as he or she uses the skin care products being purchased (preferably the products of the invention). Preferably, these images are stored by the retail store, and also provided to the consumer. This evidence is superior to relying on generalized recollection of earlier skin appearance. Moreover, it is greatly superior to relying on claims by manufacturers or other vendors. Rather, commercially available skin care products are put to the direct test of the camera by the consumer.

Preferably, a 35 mm camera is utilized to track these changes. In one embodiment, that camera is a standard 35 mm camera including a ultraviolet (UV) filter on the lens to block out ultraviolet light, and preferably also including KODAK TRI-X 400 and/or KODAK GOLD SUPER 200 film. This arrangement allows photography of the skin in greater detail. For example, the arrangement allows imaging of features to approximately 3 mm down into the skin, which is of higher resolution and quality than a non-filtered photograph.

Alternatively, any other camera for high resolution imaging of the skin can be provided. In an alternate preferred embodiment, a digital camera having an ultraviolet filter is used, for capturing a digital image that is saved onto a computer and/or floppy disk. In further embodiments, any other photographic conditions or arrangements can be provided for high image resolution as known in the photographic arts.

Preferably, in accordance with the invention, the photographic conditions are strictly controlled to further facilitate the comparison of the photographs over time. In other words, the conditions for taking the photographs, including, but not limited to, lighting, location, background, the camera, etc., are all strictly controlled and are the same for the subject from photograph to photograph. Further preferably, the conditions for developing the pictures, including, but not limited to, temperature, amount of developer, timing, etc. are also strictly controlled and are kept the same each time the film is developed for a given subject. If possible, a given technician always takes the pictures for a given subject over time, and a given technician always develops the pictures for a given subject over time, to further reduce any factors which could contribute to statistical variability in the image (i.e to qualities of the image not arising from the characteristics of the skin itself).

Having described this invention with regard to specific embodiments, it is to be understood that the description is not meant as a limitation since further embodiments, modifications and variations may be apparent or may suggest themselves to those skilled in the art. It is intended that the present application cover all such embodiments, modifications and variations.

What is claimed is:

1. A composition for the treatment of skin comprising:
 (a) retinyl palmitate polypeptide;
 (b) ascorbylmethylsilanol pectinate;
 (c) tocopheryl polypeptide;
 (d) cholecalciferol polypeptide; and
 (e) niacinimide polypeptide;
 wherein the ratio of said retinyl palmitate polypeptide to said ascorbylmethylsilanol pectinate to said tocopheryl polypeptide to said cholecalciferol polypeptide to said niacinimide polypeptide is 95:1.25:1.25:1.25.

* * * * *